a2 United States Patent
Reiffenrath et al.

US008999198B2

(10) Patent No.: US 8,999,198 B2
(45) Date of Patent: *Apr. 7, 2015

(54) COMPOUNDS FOR A LIQUID-CRYSTALLINE MEDIUM, AND THE USE THEREOF FOR HIGH-FREQUENCY COMPONENTS

(75) Inventors: Volker Reiffenrath, Rossdorf (DE); Christian Jasper, Seligenstadt (DE); Atsutaka Manabe, Bensheim (DE); Elvira Montenegro, Weinheim (DE); Detlef Pauluth, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/879,116

(22) PCT Filed: Sep. 14, 2011

(86) PCT No.: PCT/EP2011/004607
§ 371 (c)(1),
(2), (4) Date: Apr. 12, 2013

(87) PCT Pub. No.: WO2012/048774
PCT Pub. Date: Apr. 19, 2012

(65) Prior Publication Data
US 2013/0221274 A1    Aug. 29, 2013

(30) Foreign Application Priority Data
Oct. 13, 2010  (DE) .................. 10 2010 048 375

(51) Int. Cl.
| C09K 19/30 | (2006.01) |
| C09K 19/06 | (2006.01) |
| C09K 19/00 | (2006.01) |
| C07C 43/20 | (2006.01) |
| C07C 15/20 | (2006.01) |
| C07C 13/48 | (2006.01) |
| C07C 19/08 | (2006.01) |
| C07C 22/00 | (2006.01) |
| C07C 25/13 | (2006.01) |
| C07C 25/24 | (2006.01) |
| C09K 19/18 | (2006.01) |
| C09K 19/42 | (2006.01) |
| C07C 15/14 | (2006.01) |
| C09K 19/08 | (2006.01) |
| C09K 19/04 | (2006.01) |

(52) U.S. Cl.
CPC ............... *C07C 25/24* (2013.01); *C09K 19/18* (2013.01); *C09K 19/3001* (2013.01); *C09K 19/42* (2013.01); *C07C 15/14* (2013.01); *C09K 19/08* (2013.01); *C09K 19/30* (2013.01); *C09K 19/3098* (2013.01); *C09K 2019/0481* (2013.01); *C09K 2019/0485* (2013.01); *C09K 2019/188* (2013.01); *C09K 2019/3009* (2013.01); *C09K 2019/3016* (2013.01); *C09K 2019/3021* (2013.01); *C09K 2019/3037* (2013.01); *C09K 2219/11* (2013.01); *C09K 2019/301* (2013.01)

(58) Field of Classification Search
USPC ............... 252/299.01, 299.6, 299.62, 299.63; 428/1.1; 570/128, 184; 568/631; 585/25–27
See application file for complete search history.

(56) References Cited

U.S. PATENT DOCUMENTS

| 6,149,837 | A | 11/2000 | Sekine et al. | |
| 6,168,728 | B1 | 1/2001 | Miyazawa et al. | |
| 6,623,810 | B2 | 9/2003 | Sekine et al. | |
| 7,361,288 | B2 | 4/2008 | Lussem et al. | |
| 8,557,142 | B2 * | 10/2013 | Montenegro et al. | .... 252/299.63 |
| 2001/0050353 | A1 | 12/2001 | Sekine et al. | |
| 2005/0067605 | A1 | 3/2005 | Lussem et al. | |
| 2013/0292608 | A1 * | 11/2013 | Manabe et al. | .......... 252/299.62 |

FOREIGN PATENT DOCUMENTS

| DE | 19907941 A1 | 8/1999 |
| DE | 10120024 A1 | 11/2001 |
| DE | 102004029429 A1 | 2/2005 |
| EP | 0581272 A1 | 2/1994 |
| EP | 0968988 A1 | 1/2000 |

OTHER PUBLICATIONS

International Search Report for PCT/EP2011/004607 (Dec. 1, 2011).
C.S. Hsu et al., "Synthesis of Laterally Substituted Bistolane Liquid Crystals", Liquid Crystals, vol. 27, No. 2 (2000) pp. 283-287.
Z. Zhang et al., "Synthesis and Properties of Highly Birefringent Liquid Crystalline Materials: 2,5-bis(5-alkyl-2-butadinylthiophene-yl) Styrene Monomers", Liquid Crystals, vol. 37, No. 1 (Jan. 2010) pp. 69-76.
K. Liu et al., "Synthesis and Characterization of Novel Fluorinated Bistolane-Type Liquid Crystals", Liquid Crystals, vol. 28, No. 10 (2001) pp. 1463-1467.

* cited by examiner

*Primary Examiner* — Geraldina Visconti
(74) *Attorney, Agent, or Firm* — Millen, White, Zelano & Branigan, P.C.

(57) ABSTRACT

The present invention relates to 1,4-diethynylbenzene derivatives having substituents in the 2,3-position (cf. formula I, Claims), to the use thereof for high-frequency components, to liquid-crystalline media comprising the compounds, and to high-frequency components, in particular antennae, especially for the gigahertz range, comprising these media. The liquid-crystalline media serve, for example, for the phase shifting of microwaves for tuneable 'phased-array' antennae.

14 Claims, No Drawings

COMPOUNDS FOR A LIQUID-CRYSTALLINE MEDIUM, AND THE USE THEREOF FOR HIGH-FREQUENCY COMPONENTS

The present invention relates to 1,4-diethynylbenzene derivatives having substituents in the 2,3-position of the benzene ring (cf. formula I, Claims), to the use thereof for high-frequency components, to liquid-crystalline media comprising the compounds, and to high-frequency components, in particular antennae, especially for the gigahertz range, comprising these media. The liquid-crystalline media serve, for example, for the phase shifting of microwaves for tuneable 'phased-array' antennae.

Liquid-crystalline media have been used for some time in electro-optical displays (liquid crystal displays—LCDs) in order to display information.

1,4-Diethynylbenzene derivatives are proposed as liquid-crystalline components in the specifications EP 0968988 A1, DE 19907941 A1, DE 10120024 A1 and JP 08012599A. However, the specific substitution therein does not correspond to the substitution pattern of the compounds reproduced in the context of this invention.

However, liquid-crystalline media have recently also been proposed for use in components for microwave technology, such as, for example, in DE 10 2004 029 429 A and in JP 2005-120208 (A).

An industrially valuable application of liquid-crystalline media in high-frequency technology is based on their property that their dielectric properties can be controlled by a variable voltage, particularly for the gigahertz range. Thus, tuneable antennae can be designed which contain no moving parts (A. Gaebler, A. Moessinger, F. Goelden, et al., "Liquid Crystal-Reconfigurable Antenna Concepts for Space Applications at Microwave and Millimeter Waves," International Journal of Antennas and Propagation, vol. 2009, Article ID 876989, 7 pages, 2009. doi:10.1155/2009/876989).

The publication A. Penirschke, S. Müller, P. Scheele, C. Weil, M. Wittek, C. Hock and R. Jakoby: "Cavity Perturbation Method for Characterization of Liquid Crystals up to 35 GHz", 34th European Microwave Conference—Amsterdam, 545-548, describes, inter alia, the properties of the known, liquid-crystalline single substance K15 (Merck KGaA, Germany) at a frequency of 9 GHz.

1-(Phenylethynyl)tolans, also called bistolan compounds below, having an alkyl substitution on the central phenylene ring are known to the person skilled in the art. For example, the publication S.-T. Wu, C.-S. Hsu, K.-F. Shyu *Appl. Phys. Lett.* (1999), 74 (3), 344-346, discloses various liquid-crystalline bistolan compounds having a lateral methyl group, of the formula

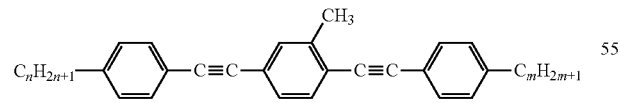

Besides liquid-crystalline bistolan compounds of this type having a lateral methyl group, C. S. Hsu, K. F. Shyu, Y. Y. Chuang, S.-T. Wu *Liq. Cryst.* (2000), 27 (2), 283-287, also discloses corresponding compounds having a lateral ethyl group and proposes the use thereof, inter alia, in "liquid crystal optically phased arrays".

DE 10 2004 029 429 A (cf. above) describes the use of conventional liquid-crystal media in microwave technology, inter alia in phase shifters. Liquid-crystalline media have already been investigated therein with respect to their properties in the corresponding frequency range.

However, the compositions or individual compounds known to date are generally afflicted with disadvantages. Most of them result, besides other deficiencies, in disadvantageously high losses and/or inadequate phase shifts or inadequate material quality.

For use in high-frequency technology, liquid-crystalline media having particular, hitherto rather unusual, non-standard properties, or combinations of properties, are required.

Thus, novel components for liquid-crystalline media having improved properties are necessary. In particular, the loss in the microwave range must be reduced and the material quality ($\eta$) must be improved. For tuneable antennae, liquid-crystalline media having a fast reaction time to a change in the voltage between the electrodes of the cell are also required.

In addition, there is a need to improve the low-temperature behaviour of the components. Both an improvement in the operating properties and also in the shelf life is necessary here.

There is therefore a considerable demand for liquid-crystalline media having suitable properties for corresponding practical applications.

Surprisingly, it has been found that the compounds according to the invention having two substituents in the ortho position on one aromatic ring have a significantly higher clearing point (transition from the nematic phase into the isotropic phase) compared with a corresponding monosubstituted compound or a disubstituted compound in which the substituents are not arranged in the ortho position to one another. At the same time, the rotational viscosity ($\gamma_1$) is significantly lower than in the comparative compounds having fewer substituents or without an ortho position of the substituents. This effect arises in compounds in which the ring systems are kept at distance by rigid ethynylene bridges. Utilising this effect, it has now been found, surprisingly, that liquid-crystalline media having a suitable, nematic phase range and high $\Delta n$ which do not have the disadvantages of the materials of the prior art or at least only do so to a considerably reduced extent can be achieved with the compounds according to the invention.

The invention relates to compounds of the formula I,

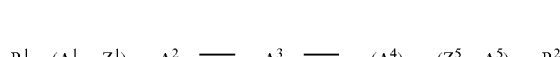

in which
$A^3$ denotes

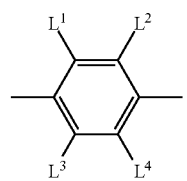

$L^1, L^2$ each, independently of one another, denote branched or unbranched alkyl, alkenyl or alkynyl having 1 to 12 C atoms, in which, in addition, one or more "—$CH_2$—" groups may be replaced, independently of one another, by O, substituted or unsubstituted cycloalkyl, cycloalkenyl, substituted or unsubstituted phenyl, substituted or unsubstituted arylethynyl, fluorinated alkyl or alkenyl, fluorinated alkoxy or alkenyloxy, F, Cl, Br, CN, NCS or $SF_5$, $L^3$, $L^4$ are defined like $L^{1/2}$ or denote H, $R^1$ and $R^2$, independently of one another, denote a halogenated or unsubstituted alkyl radical having 1 to 15 C atoms, where, in addition, one or more $CH_2$ groups in these radicals may each be replaced, independently of one another, by —C≡C—, —CH=CH—, —CF=CF—, —CF=CH—, —CH=CF—, —(CO)— and —O— in such a way that O atoms are not linked directly to one another, F, Cl, Br, CN, $CF_3$, $OCF_3$, NCS or $SF_5$, $R^2$ also denotes H, $A^1$, $A^2$, $A^4$, $A^5$ each, independently of one another, denote a) 1,4-phenylene, in which one or more, preferably one to two, CH groups may be replaced by N, b) trans-1,4-cyclohexylene or cyclohexenylene, in which, in addition, one or two non-adjacent $CH_2$ groups may be replaced by —O— and/or —S—, and in which H may be replaced by F, c) a radical of the formula

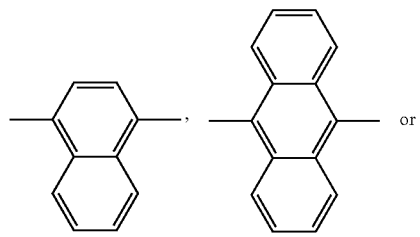

or

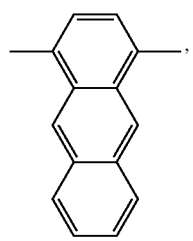

or d) a radical from the group 1,4-bicyclo[2.2.2]octylene, cyclo-butane-1,3-diyl, spiro[3.3]heptane-2,6-diyl, thiophene-2,5-diyl, thiophene-2,4-diyl, furan-2,5-diyl, furan-2,4-diyl,

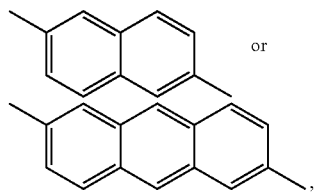

and in which, in groups a), b), c) and d), one or more H atoms may, in addition, be replaced by Br, Cl, F, CN, —NCS, —SCN, $SF_5$, $C_1$-$C_{10}$ alkyl, $C_1$-$C_{10}$ alkoxy or a mono- or polyfluorinated $C_1$-$C_{10}$ alkyl or alkoxy group, and where at least one radical from $A^1$ to $A^5$, preferably from $A^2$, $A^3$ and $A^4$, represents a radical according to a), k denotes 0 or 1, $Z^1$, $Z^5$, independently of one another, denote a single bond, —C≡C—, —CH=CH—, —$CH_2$O—, —(CO)O—, —$CF_2$O—, —$CF_2CF_2$—, —$CH_2CF_2$—, —$CH_2CH_2$—, —$(CH_2)_4$—, —CH=CF— or —CF=CF—, where asymmetrical bridges may be oriented to both sides, where, for k=0, $Z^5$ denotes a single bond, and m, n, independently of one another, denote 0, 1 or 2.

The compounds according to the invention have a high clearing point, a low melting point, extremely high optical anisotropy (Δn). Fast response times are achieved by a surprisingly low rotational viscosity $γ_1$. A phase shifter can thus adjust faster. The relatively low loss factor in the microwave spectrum is also advantageous. The compounds, alone or in a mixture with further mesogenic components, have a nematic phase over a broad temperature range. These properties make them particularly suitable for use in components for high-frequency technology, in particular in liquid-crystalline phase shifters. Liquid-crystalline media according to the invention have the corresponding properties, for example a broad phase range, fast response time, and in addition good low-temperature stability.

Preferred compounds of the formula I are characterised by the choice of one or more of the following parameters:

The index m is preferably 0 or 1, particularly preferably 0. The index n is preferably 0 or 1, particularly preferably 0. m+n is preferably 0 or 1.

The ring groups $A^1$ and $A^5$ are, independently of one another, preferably a 1,4-phenylene, in which, in addition, one or more H atoms may be replaced by Br, Cl, F, CN, alkyl ($C_1$-$C_{10}$), methoxy or a mono- or polyfluorinated methyl or methoxy group.

The bridging groups $Z^1$ and $Z^5$ are, independently of one another, preferably a single bond, —C≡C—, —CF=CF— or —CH=CH—, particularly preferably a single bond.

Preferred structures are therefore selected from I-1 to I-3:

I-1

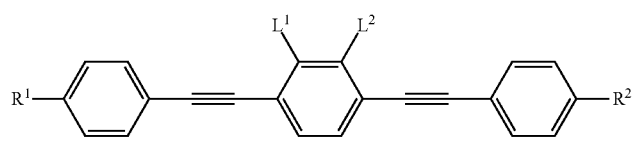

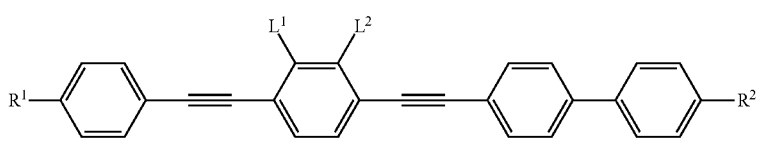

I-2

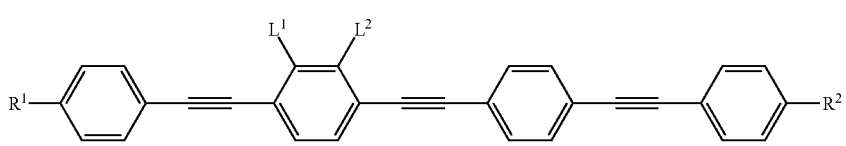

I-3

One of the radicals $R^1$ or $R^2$, preferably $R^1$, preferably denotes a straight-chain alkyl radical having 1 to 15 C atoms, where, in addition, one or more $CH_2$ groups in these radicals may each be replaced, independently of one another, by —C≡C—, —CH=CH—, —(CO)O—, —O(CO)—, —(CO)—, —O— in such a way that O atoms are not linked directly to one another. The groups $R^1$ and $R^2$ are preferably both an alkyl having 2 to 7 C atoms. In this case, $R^1$ and $R^2$ denote, for example, propyl and hexyl or butyl and butyl, furthermore propyl and pentyl, propyl and hexyl or butyl and pentyl.

The groups $L^1$ and $L^2$ preferably each, independently of one another, denote F, Cl, CN, branched or unbranched alkyl, alkenyl or alkynyl having 1 to 8 C atoms, in which, in addition, one or more "—$CH_2$—" groups may be replaced, independently of one another, by O, substituted or unsubstituted cycloalkyl, cycloalkenyl, fluorinated alkyl or alkenyl, fluorinated alkoxy or alkenyloxy, each having up to 8 C atoms, particularly preferably F, Cl, alkyl having 1 to 5 C atoms, alkenyl having 2 to 5 C atoms, cyclopropyl or cyclobutyl. Preferably, one group from $L^{1/2}$ is an F, methyl, ethyl, cyclopropyl or Cl, particularly preferably F, and the other group is as defined above, or is preferably F, Cl, alkyl having 1 to 5 C atoms, alkenyl having 2 to 5 C atoms, cyclopropyl or cyclobutyl.

The groups $L^3$ and $L^4$ are preferably both H or both not H, particularly preferably are both H.

The ring group $A^3$ preferably has a part-structure selected from the following formulae:

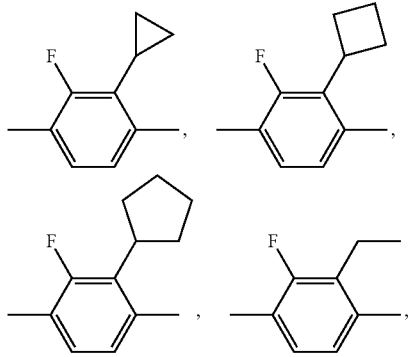

-continued

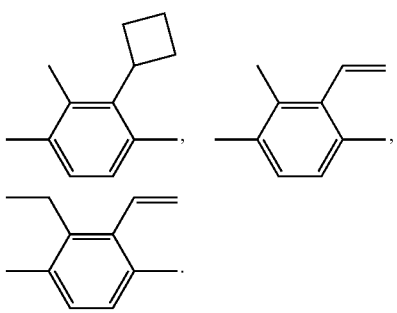

Preferred embodiments of the invention are therefore selected from the following illustrative structures:

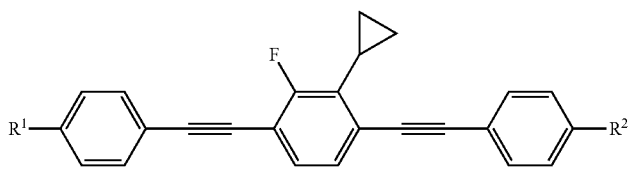

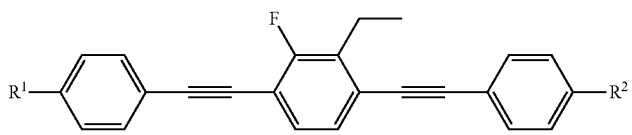

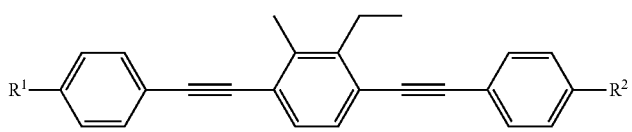

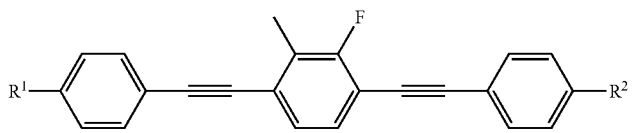

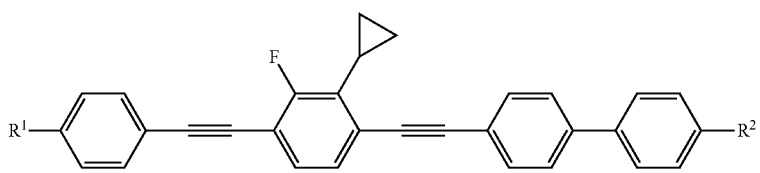

in which $R^1$ and $R^2$ independently denote an alkyl radical having 2 to 7 C atoms, for example a propyl or hexyl radical or each denote a propyl, butyl, pentyl or hexyl radical.

For compounds of the formula I in which k=0, $Z^5$ denotes a single bond. For compounds of the formula I in which k=0, the variable n furthermore preferably adopts the value 0, and the radical $R^2$ preferably denotes a halogenated or unsubstituted alkyl radical having 1 to 15 C atoms, where, in addition, one or more $CH_2$ groups in this radical may each be replaced, independently of one another, by —C≡C—, —CH=CH—, —CF=CF—, —CF=CH— and —CH=CF—, or denotes CN, $CF_3$, NCS or $SF_5$. $R^2$ in these compounds particularly preferably denotes an unsubstituted alkyl radical having 1 to 15 C atoms, CN or NCS.

The compounds of the formula I can advantageously be obtained in accordance with the following general reaction schemes (Reaction Schemes I to VIII). The parameters $R^{1/2}$, $A^{1-5}$, $Z^{1/5}$, m and n therein are as defined above and below. R has the meaning of $R^{1/2}$.

Reaction Scheme I. $A^2 = A^4$, $Z^5 = Z^1$, $A^5 = A^1$, m = n:

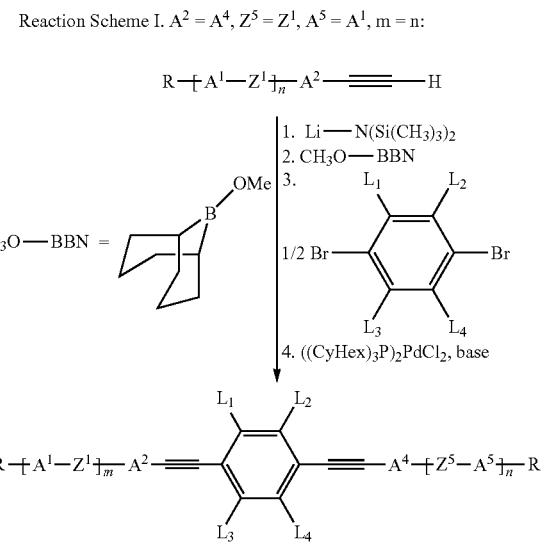

Reaction Scheme II (asymmetrical substitution):

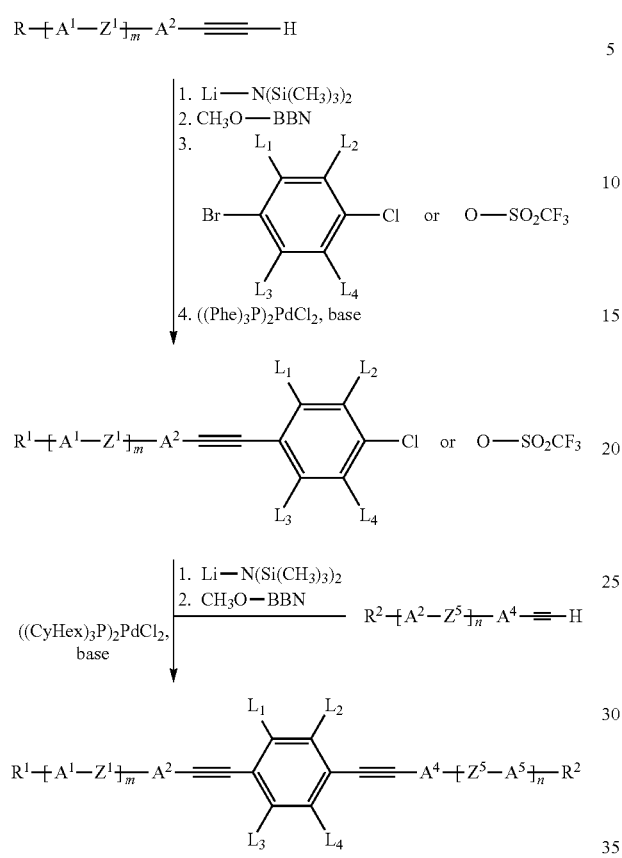

In Reaction Schemes III to VII, the synthesis of variously substituted rings $A^3$ is reproduced. The phenylalkynyl radicals here can be generalised to any desired radicals ≡-$A^2$-$(Z^1$-$A^1)_m$-$R^1$ or ≡-$(A^4)_k$-$(Z^5$-$A^5)_n$-$R^2$.

Reaction Scheme III (Li—TMP: Li tetramethylpiperidide):

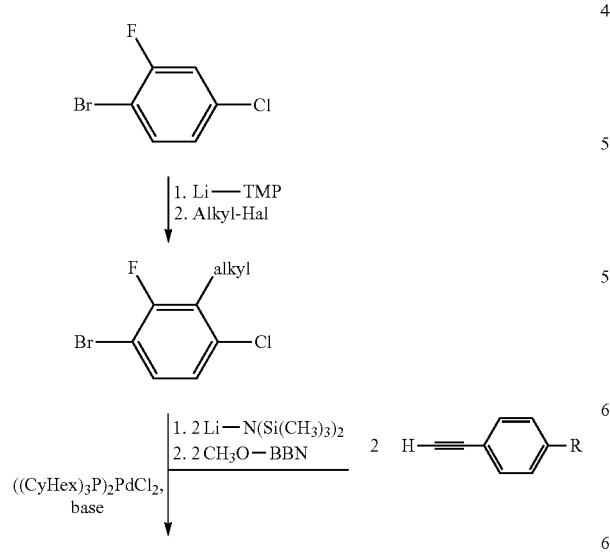

Reaction Scheme IV (LDA: Li diisopropylamide):

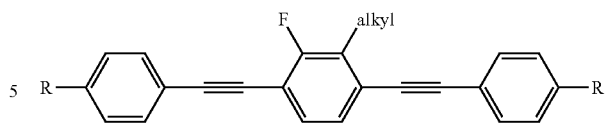

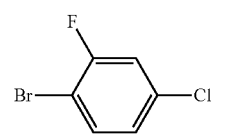

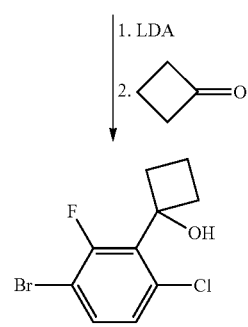

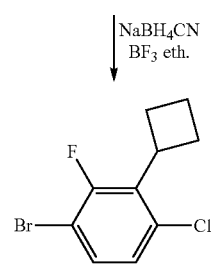

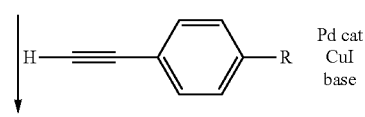

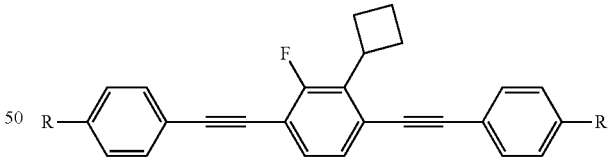

Reaction Scheme V:

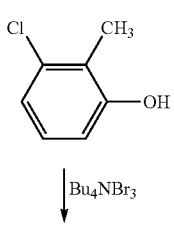

-continued
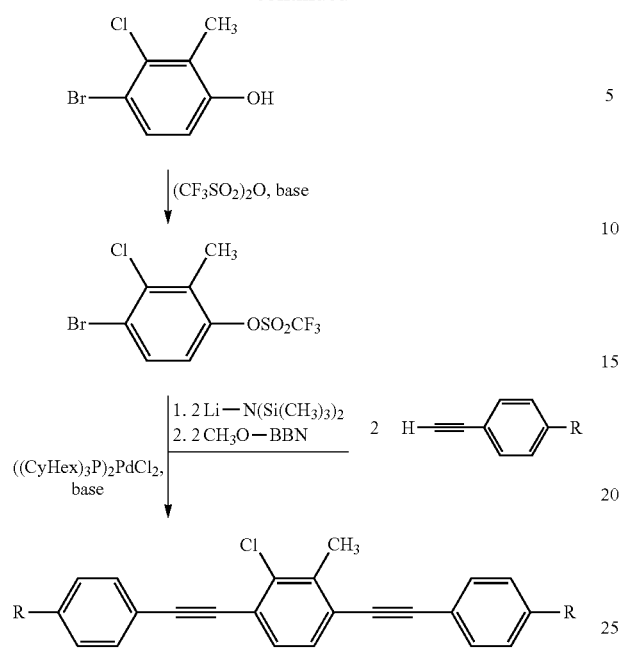
Reaction Scheme VI:
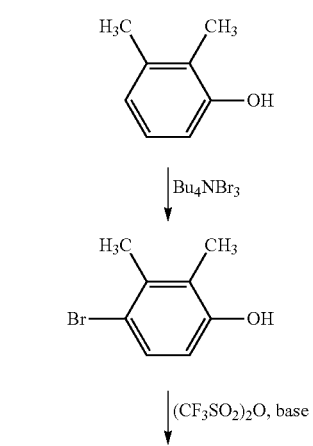
Reaction Scheme VII:
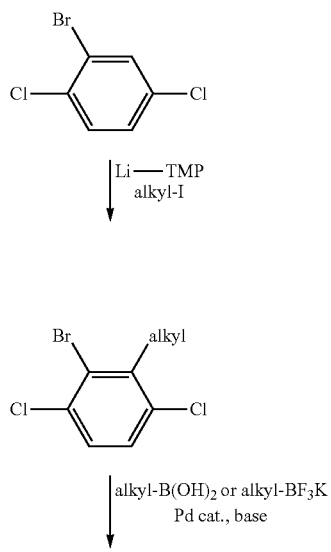
Reaction Scheme VIII (k = 0):
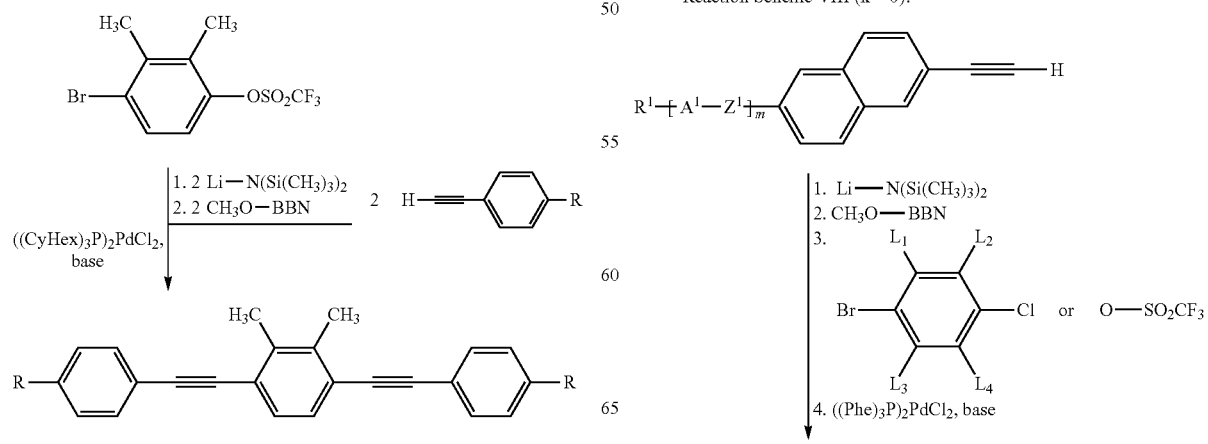

-continued

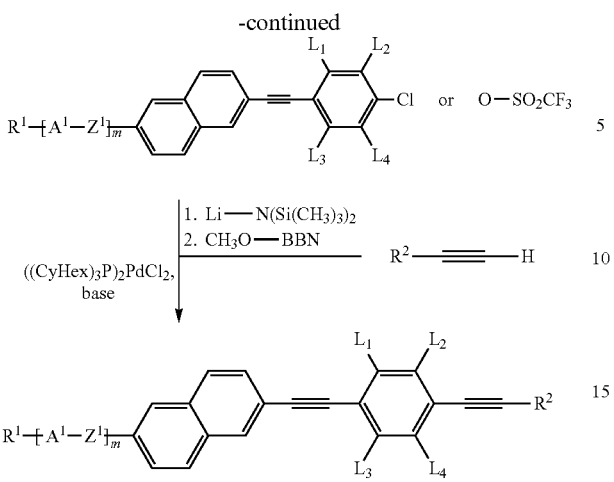

The liquid-crystalline media in accordance with the present invention comprise one or more compounds of the formula I and optionally at least one further, preferably mesogenic compound. The liquid-crystal medium therefore preferably comprises two or more compounds which are preferably liquid-crystalline. Preferred media comprise the preferred compounds of the formula I.

Further components of the liquid-crystalline media are preferably selected from the compounds of the formula II:

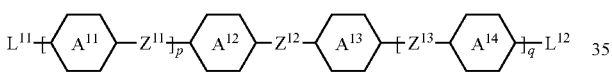

II in which $L^{11}$ denotes $R^{11}$ or $X^{11}$, $L^{12}$ denotes $R^{12}$ or $X^{12}$, $R^{11}$ and $R^{12}$, independently of one another, denote unfluorinated alkyl or unfluorinated alkoxy having 1 to 17, preferably having 3 to 10, C atoms or unfluorinated alkenyl, unfluorinated alkynyl, unfluorinated alkenyloxy or unfluorinated alkoxyalkyl having 2 to 15, preferably 3 to 10, C atoms, preferably alkyl or unfluorinated alkenyl, $X^{11}$ and $X^{12}$, independently of one another, denote F, Cl, Br, —CN, —NCS, —SCN, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl, p, q independently denote 0 or 1, $Z^{11}$ to $Z^{13}$, independently of one another, denote trans-CH=CH—, trans-CF=CF—, —C≡C— or a single bond, and

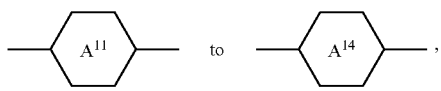

independently of one another, denote

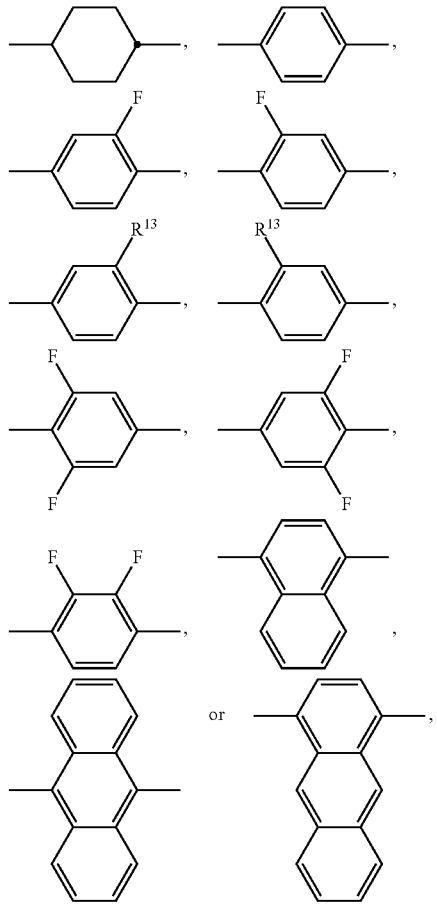

where $R^{13}$ denotes Cl, $C_{1-5}$ alkyl, $C_{1-5}$ alkenyl or $C_{3-6}$ cycloalkyl.

In a preferred embodiment of the present invention, the liquid-crystalline media comprise one or more compounds of the formula I and one or more compounds of the formula II.

The liquid-crystalline media in accordance with the present application preferably comprise in total 5 to 95%, preferably 10 to 90% and particularly preferably 15 to 80%, of compounds of the formula I.

The liquid-crystalline media in accordance with the present invention preferably comprise, more preferably predominantly consist of, even more preferably essentially consist of and very preferably completely consist of compounds selected from the group of the compounds of the formulae I and II.

In this application, "comprise" in connection with compositions means that the entity in question, i.e. the medium or the component, comprises the component or components or compound or compounds indicated, preferably in a total concentration of 10% or more and very preferably 20% or more.

In this connection, "predominantly consist of" means that the entity in question comprises 55% or more, preferably 60% or more and very preferably 70% or more, of the component or components or compound or compounds indicated.

In this connection, "essentially consist of" means that the entity in question comprises 80% or more, preferably 90% or more and very preferably 95% or more, of the component or components or compound or compounds indicated.

In this connection, "completely consist of" means that the entity in question comprises 98% or more, preferably 99% or more and very preferably 100.0%, of the component or components or compound or compounds indicated.

The liquid-crystalline media in accordance with the present application preferably comprise in total 10 to 100%, preferably 20 to 95% and particularly preferably 25 to 90%, of compounds of the formulae I and II.

In accordance with the present invention, the compounds of the formula II are preferably used in a total concentration of 10% to 90%, more preferably 15% to 85%, even more preferably 25% to 80% and very preferably 30% to 75%, of the mixture as a whole.

In addition, the liquid-crystalline media may comprise further additives, such as stabilisers, chiral dopants and nanoparticles. The individual, added compounds are employed in concentrations of 0.005 to 6%, preferably 0.1 to 3%. The total concentration of these further constituents is in the range from 0% to 10%, preferably 0.1% to 6%, based on the mixture as a whole. However, the concentration data for the remaining constituents of the liquid-crystal mixtures, i.e. the liquid-crystalline or mesogenic compounds, are indicated without taking into account the concentration of these additives.

The liquid-crystalline media preferably comprise 0 to 10% by weight, in particular 0.01 to 5% by weight and particularly preferably 0.1 to 3% by weight, of stabilisers. The media preferably comprise one or more stabilisers selected from 2,6-di-tert-butylphenols, 2,2,6,6-tetramethylpiperidines or 2-benzotriazol-2-ylphenols. These assistants are known to the person skilled in the art and are commercially available, for example as light stabilisers.

An embodiment of the invention is therefore also a process for the preparation of a liquid-crystal medium which is characterised in that one or more compounds of the formula I are mixed with one or more further compounds and optionally with one or more additives. The further compounds are preferably selected from the compounds of the formula II, as indicated above, and optionally one or more further compounds.

In the present application, the expression dielectrically positive describes compounds or components where $\Delta\epsilon > 3.0$, dielectrically neutral describes those where $-1.5 \leq \Delta\epsilon \leq 3.0$ and dielectrically negative describes those where $\Delta\epsilon < -1.5$. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 µm. The voltage applied is a rectangular wave having a frequency of 1 kHz and an effective value of typically 0.5 V to 1.0 V, but it is always selected to be below the capacitive threshold of the respective test mixture.

$\Delta\epsilon$ is defined as $(\epsilon_\| - \epsilon_\perp)$, whereas $\epsilon_{average}$ is $(\epsilon_\| + 2\epsilon_\perp)/3$.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The term threshold voltage in the present application refers to the optical threshold and is quoted for 10% relative contrast ($V_{10}$), and the term saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties that are typical for liquid crystals are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\epsilon$) is determined at a frequency of 1 kHz. The threshold voltages, as well as all other electro-optical properties, are determined using test cells produced at Merck KGaA, Germany. The test cells for the determination of $\Delta\epsilon$ have a cell thickness of approximately 20 µm. The electrode is a circular ITO electrode having an area of 1.13 cm$^2$ and a guard ring. The orientation layers are SE-1211 from Nissan Chemicals, Japan, for homeotropic orientation ($\epsilon_\|$) and polyimide AL-1054 from Japan Synthetic Rubber, Japan, for homogeneous orientation ($\epsilon_\perp$). The capacitances are determined using a Solatron 1260 frequency response analyser using a sine wave with a voltage of 0.3 V$_{rms}$. The light used in the electro-optical measurements is white light. A set-up using a commercially available DMS instrument from Autronic-Melchers, Germany, is used here. The characteristic voltages are determined under perpendicular observation. The threshold ($V_{10}$), mid-grey ($V_{50}$) and saturation ($V_{90}$) voltages are determined for 10%, 50% and 90% relative contrast, respectively.

The liquid-crystalline media are investigated with respect to their properties in the microwave frequency range as described in A. Penirschke et al. "Cavity Perturbation Method for Characterization of Liquid Crystals up to 35 GHz", 34$^{th}$ European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) or quartz capillary. The capillary has an internal radius of 180 µm and an external radius of 350 µm. The effective length is 2.0 cm. The filled capillary is introduced into the centre of the cavity with a resonance frequency of 30 GHz. This cavity has a length of 6.6 mm, a width of 7.1 mm and a height of 3.6 mm. The input signal (source) is then applied, and the result of the output signal is recorded using a commercial vector network analyser. For other frequencies (e.g. 19 GHz), the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in the above-mentioned publication A. Penirschke et al., 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

The dielectric anisotropy in the microwave range is defined as $$\Delta \epsilon_r \equiv (\epsilon_{r,\|} - \epsilon_{r,\perp}).$$

The modulatability or tuneability ($\tau$) is defined as $$\tau \equiv (\Delta \epsilon_r / \epsilon_{r,\|}).$$

The material quality ($\eta$) is defined as $$\eta \equiv (\tau / \tan \delta_{\epsilon r, max.}),$$

with the maximum dielectric loss factor $\tan \delta_{\epsilon r, max.}$:

$$\tan \delta_{\epsilon r, max.} \equiv \max. \{\tan \delta_{\epsilon r, \perp}; \tan \delta_{\epsilon r, \|}\}$$

which arises from the maximum value of the measured values for $\tan \delta_{\epsilon r}$.

The material quality ($\eta$) of the preferred liquid-crystal materials is 6 or more, preferably 8 or more, preferably 10 or more, preferably 15 or more, preferably 17 or more, particularly preferably 20 or more and very particularly preferably 25 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

The liquid-crystal media according to the invention preferably have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 180° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a cell thickness of 5 µm for at least 100 hours. At high temperatures, the clearing point is measured in capillaries by conventional methods.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The $\Delta\epsilon$ of the liquid-crystal medium in accordance with the invention, at 1 kHz and 20° C., is preferably 1 or more, more preferably 2 or more and very preferably 3 or more.

The $\Delta n$ of the liquid-crystal media in accordance with the present invention, at 589 nm (Na$^D$) and 20° C., is preferably in the range from 0.20 or more to 0.90 or less, more preferably in the range from 0.25 or more to 0.90 or less, even more preferably in the range from 0.30 or more to 0.85 or less and very particularly preferably in the range from 0.35 or more to 0.80 or less.

In a preferred embodiment of the present application, the $\Delta n$ of the liquid-crystal media in accordance with the present invention is 0.45 or more, preferably 0.50 or more, and particularly preferably 0.55 or more.

Furthermore, the liquid-crystal media according to the invention are characterised by high anisotropies in the microwave range. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

The liquid crystals employed are either individual substances or mixtures. They preferably have a nematic phase.

In the present application, the term compounds means both one compound and a plurality of compounds, unless expressly stated otherwise.

Preferred components which comprise a liquid-crystal medium or at least one compound in accordance with the invention are phase shifters, varactors, antenna arrays (for example for radio, mobile communications, microwave/radar and other data transmission), 'matching circuit adaptive filters' and others. Preference is given to components for high-frequency technology, as defined above. Preference is also given to components which can be modulated by different applied electrical voltages. Very particularly preferred components are phase shifters. In preferred embodiments, a plurality of phase shifters are functionally connected, giving, for example, a phase-controlled group antenna, generally referred to as 'phased array' antenna. A group antenna uses the phase shift of the transmitting or receiving elements arranged in a matrix in order to achieve bundling through interference. A parallel arrangement of phase shifters in row or grid form enables the construction of a so-called 'phased array', which can serve as tuneable transmitting or receiving antenna for high frequencies (for example gigahertz range). Phased array antennae according to the invention have a very broad usable reception cone.

Preferred applications are radar installations and data transmission equipment on manned or unmanned vehicles from the automobile, shipping, aircraft, space travel and satellite technology areas.

For the production of suitable components, in particular phase shifters, a liquid-crystalline medium according to the invention is typically introduced into rectangular cavities having a thickness of less than 1 mm, a width of several mm and a length of several centimeters. The cavities have opposing electrodes mounted along two long sides. Such arrangements are familiar to the person skilled in the art. Through application of a variable voltage, the dielectric properties of the liquid-crystalline medium can be tuned during operation of the antenna in order to set different frequencies or directions of an antenna.

The term "halogen" or "halogenated" stands for F, Cl, Br and I, particularly for F and Cl and in particular for F.

The term "alkyl" preferably encompasses straight-chain and branched alkyl groups having 1 to 15 carbon atoms, in particular the straight-chain groups methyl, ethyl, propyl, butyl, pentyl, hexyl and heptyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, C₅- to C₇-4-alkenyl, C₆- to C₇-5-alkenyl and C₇-6-alkenyl, in particular C₂- to C₇-1E-alkenyl, C₄- to C₇-3E-alkenyl and C₅- to C₇-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "alkoxy" preferably encompasses straight-chain radicals of the formula $C_nH_{2n+1}$—O—, in which n denotes 1 to 10. n is preferably 1 to 6. Preferred alkoxy groups are, for example, methoxy, ethoxy, n-propoxy, n-butoxy, n-pentoxy, n-hexoxy, n-heptoxy, n-octoxy, n-nonoxy, n-decoxy.

The term "oxaalkyl" or "alkoxyalkyl" preferably encompasses straight-chain radicals of the formula $C_nH_{2n+1}$—O—$(CH_2)_m$, in which n and m each, independently of one another, denote 1 to 10. Preferably, n is 1 and m is 1 to 6.

The term "fluorinated alkyl radical" preferably encompasses mono- or polyfluorinated radicals. Perfluorinated radicals are included. Particular preference is given to $CF_3$, $CH_2CF_3$, $CH_2CHF_2$, $CHF_2$, $CH_2F$, $CHFCF_3$ and $CF_2CHFCF_3$.

The term "fluorinated alkoxy radical" encompasses mono- or polyfluorinated radicals. Perfluorinated radicals are preferred. Particular preference is given to the $OCF_3$ radical.

The term "substituted cycloalkyl" encompasses cycloalkyl which is mono- or polysubstituted by alkyl, in particular alkyl having 1 to 8 carbon atoms.

The term "substituted phenyl" encompasses phenyl which is mono- or polysubstituted by a group defined like R¹, in particular phenyl which is substituted by F, Cl, alkyl or alkoxy.

In the present application, high-frequency technology means applications having frequencies in the range from 1 MHz to 10 THz, preferably from 1 GHz to 3 THz, more preferably from 2 GHz to 1 THz, particularly preferably from 5 to 300 GHz. The application is preferably in the microwave spectrum or adjacent regions which are suitable for message transmission, in which phased array modules can be used in transmitting or receiving antennae.

The liquid-crystal media according to the invention consist of one or more compounds, preferably 2 to 30, more preferably 3 to 20 and very preferably 3 to 16, compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called pre-mixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present application and in the following examples, the structures of the liquid-crystal compounds are indicated by means of acronyms, where the transformation into chemical formulae is carried out in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents R¹*, R²*, L¹* and L²*:

| Code for R¹*, R²*, L¹*, L²*, L³* | R¹* | R²* | L¹* | L²* |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |
| nOCF₃ | $C_nH_{2n+1}$ | OCF₃ | H | H |
| nOCF₃.F | $C_nH_{2n+1}$ | OCF₃ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

Suitable mixture components are given in Tables A and B.

TABLE A

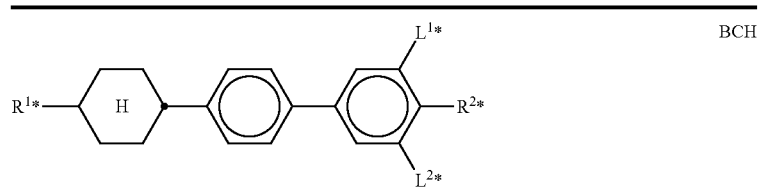

BCH

TABLE A-continued
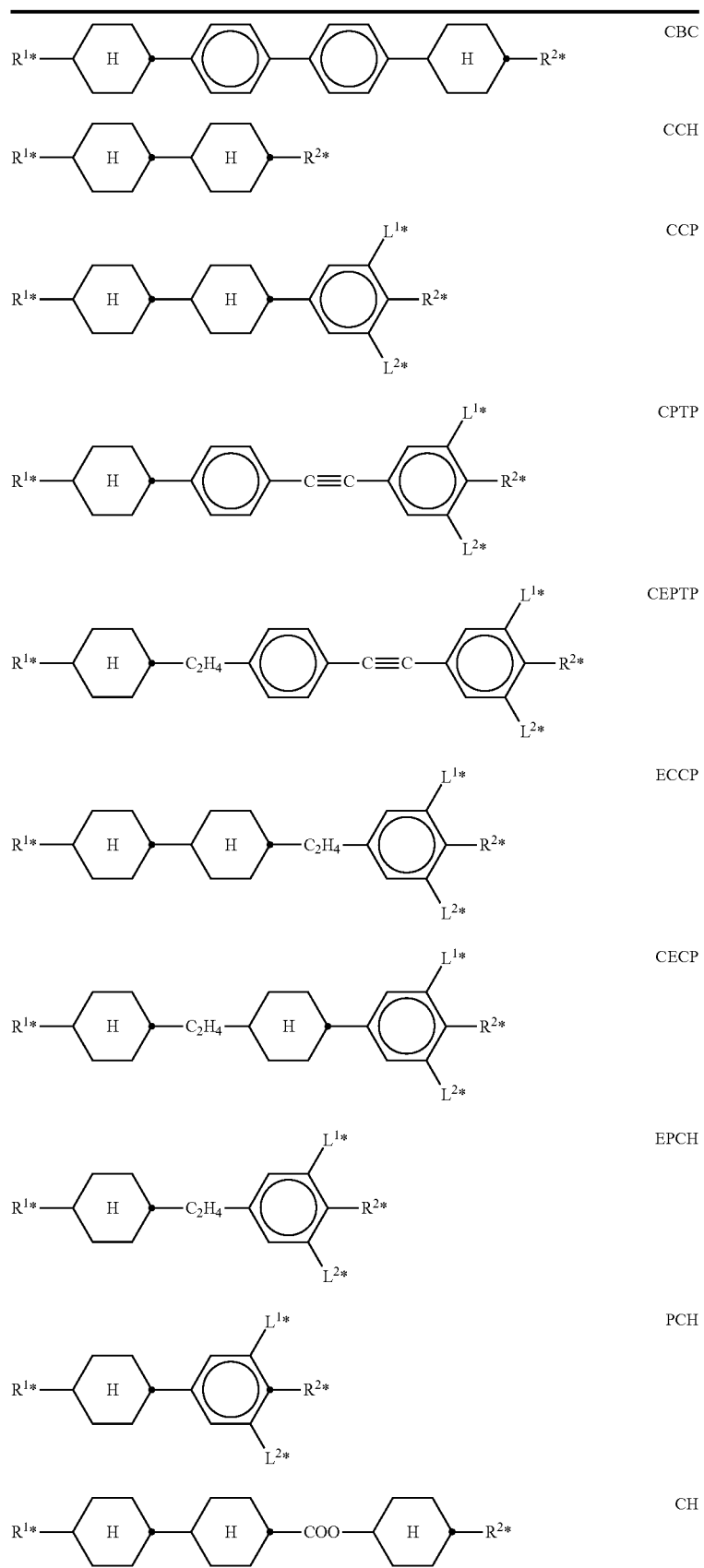

TABLE A-continued

| Structure | Code |
|---|---|
| R¹*—⌬—C≡C—⌬(L¹*)(L²*)—R²* | PTP |
| R¹*—H—H—COO—⌬—H—R²* | CCPC |
| R¹*—H—H—COO—⌬—R²* | CP |
| R¹*—H—C₂H₄—⌬—⌬(L¹*)(L²*)—R²* | BECH |

TABLE B

| Structure | Code |
|---|---|
| $C_nH_{2n+1}$—H—⌬—⌬(F)—⌬—H—$C_mH_{2m+1}$ | CBC-nmF |
| $C_nH_{2n+1}$—⌬—⌬(F)—⌬—$C_mH_{2m+1}$ | PGP-n-m |
| $C_nH_{2n+1}$—H—⌬(F)—⌬(F)—F | CGG-n-F |
| $C_nH_{2n+1}$—H—⌬—⌬(F)—⌬—$C_mH_{2m+1}$ | CPGP-n-m |
| $C_nH_{2n+1}$—⌬—⌬—⌬(F)(F)—⌬(F)—F | PPGU-n-F |
| $C_nH_{2n+1}$—⌬(F)—⌬(F)—⌬—F | GGP-n-F |

TABLE B-continued

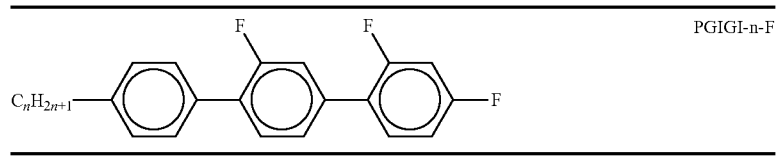

PGIGI-n-F

The following examples illustrate the present invention without limiting it in any way.

However, it becomes clear to the person skilled in the art from the physical properties what properties can be achieved and in what ranges they can be modified. In particular, the combination of the various properties which can preferably be achieved is thus well defined for the person skilled in the art.

Abbreviations used:
DMPU 1,3-dimethyl-3,4,5,6-tetrahydro-2(1H)-pyrimidinone
DBU 1,8-diazabicyclo[5.4.0]undec-7-ene or 2,3,4,6,7,8,9,10-octahydropyrimido[1,2-a]azepine (IUPAC)

EXAMPLES

The acetylenes and boronic acids employed are commercially available or can be prepared analogously to Schemes I to VIII or to known syntheses. The radicals "$C_4H_9$" stand for unbranched n-butyl radicals. A corresponding situation applies to $C_3H_7$, $C_6H_{13}$, etc.

Synthesis Example 1

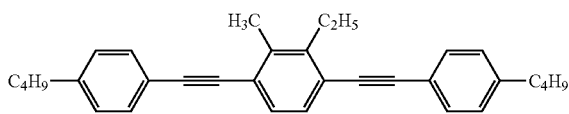

Step 1.1

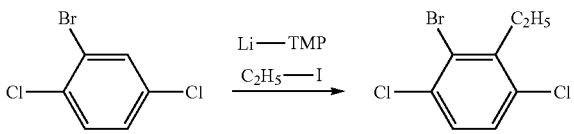

25.4 g of 2-bromo-1,4-dichlorobenzene, 8.9 ml of iodoethane and 13.3 ml of DMPU are dissolved in 230 ml of THF, and a solution of 16.2 g of lithium tetramethylpiperidide in THF is added dropwise at −70° C. After a further 2 h at −70° C., the reaction mixture is allowed to warm to ambient temperature, and the batch is hydrolysed using water and worked up by extraction. The crude product is purified by fractional distillation.

b.p.: 73° C./0.1 bar. Colourless liquid.

Step 1.2

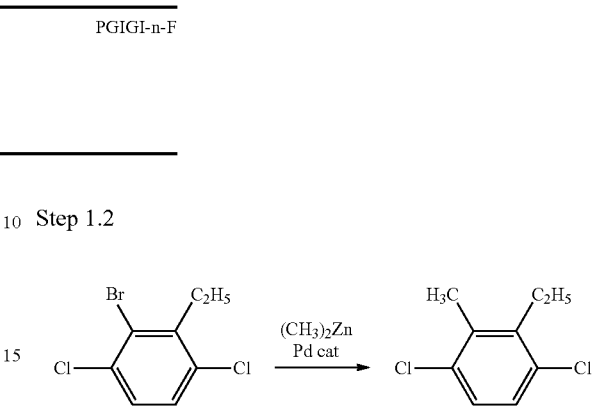

12.5 ml of a 5% solution of methyllithium in diethyl ether are added to 2.4 g of anhydrous zinc bromide in 50 ml of THF at 25-40° C. 0.3 g of $PdCl_2$— dppf, bis(diphenylphosphinoferrocene)palladium dichloride, is then added, the mixture is heated to the boil, and 4.6 g of the product from step 1.1, dissolved in a little THF, are added dropwise. The reaction mixture is subsequently heated under reflux for 15 h. The batch is hydrolysed using water and worked up by extraction. The crude product is purified by chromatography (pentane/silica gel). Colourless liquid.

Step 1.3

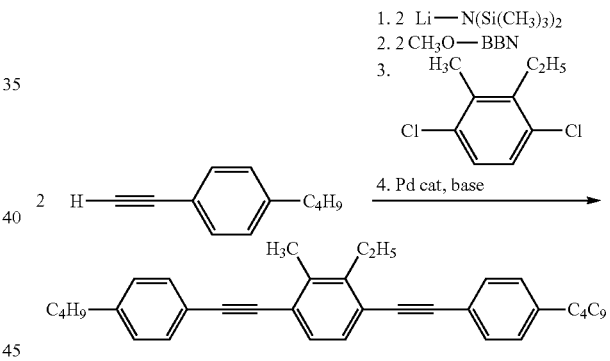

2.4 g of 4-butylphenylacetylene are initially introduced in 30 ml of THF and cooled to −78° C. 14.3 ml of a 1 M solution of lithium bis(trimethylsilyl)amide in hexane are added dropwise to this solution, and the mixture is allowed to react at −78° C. for a further 1 h. 14.3 ml of a 1 M solution of methoxy-9-BBN are then added dropwise, and the mixture is stirred at −78° C. for a further 2 h. In a second apparatus, 1.0 g of the product from the last step, dissolved in 40 ml of THF, is initially introduced with the catalyst comprising 0.2 g of tris(dibenzylideneacetone)dipalladium and 0.35 g of 2-dicyclohexylphosphino-2',6'-dimethoxybiphenyl, and the reaction solution from the first reaction is added at room temperature. The mixture is heated at the boil for 15 h. The batch is hydrolysed using water and worked up by extraction. The crude product is purified by chromatography (pentane/silica gel). Recrystallisation from pentane gives the purified title product.

C 45 N 180 I

Δ∈=+1.4

Δn=0.412

Comparative Example 1

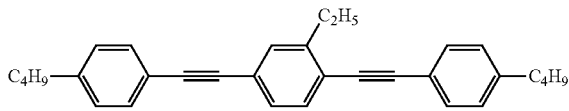

C 29 N 119 I
Δ∈=+1.7
Δn=0.402

Synthesis Example 2

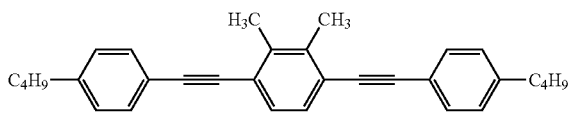

The compound is prepared analogously to Example 1.
C 118 N 222 I
Δ∈=+2.6
Δn=0.435
$\gamma_1$=889 mPa·s Synthesis Example 3

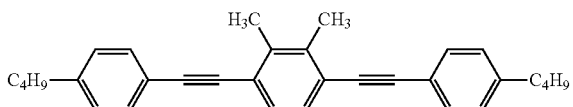

The compound is prepared analogously to Example 1.
C 167 N 225 I
Δ∈=+2.3
Δn=0.423
$\gamma_1$=1361 mPa·s Synthesis Example 4

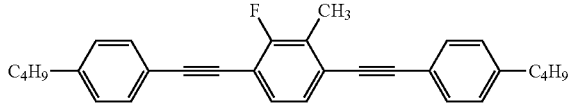

The compound is prepared analogously to Example 1.
C 90 N 194 I
Δ∈=+3.0
Δn=0.435
$\gamma_1$=647 mPa·s Comparative Example 2

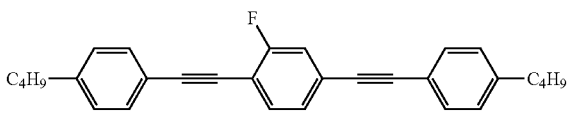

C 93 N 188.5 I
Δ∈4.1
Δn 0.452
$\gamma_1$=374 mPa·s

Synthesis Example 5

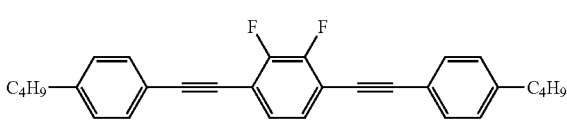

The compound is prepared analogously to Example 1.
C 96 N 199 I
Δ∈=−1.4
Δn=0.443
$\gamma_1$=308 mPa·s Synthesis Example 6

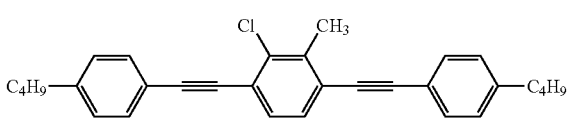

The compound is prepared analogously to Example 1.
C 92 N 205 I
Δ∈=+3.1
Δn=0.429

Synthesis Example 7

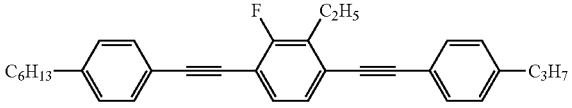

The compound is prepared analogously to Example 1.
C 53 N 144 I
Δ∈=+2.5
Δn=0.401
$\gamma_1$=1746 mPa·s Comparative Example 3

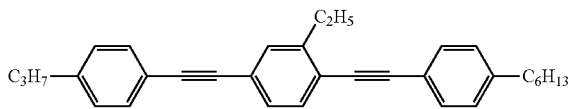

C 60 N 122 I
ΔΕ=+1.7
Δn=0.394
γ₁=1891 mPa·s

Synthesis Example 8

(1)

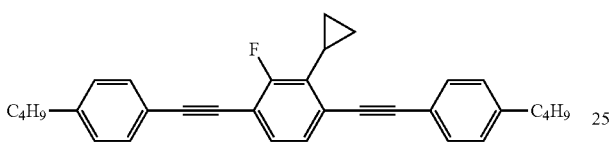

Compound (1) is prepared analogously to Example 1 and used in Mixture Example 1.
Tg −49 C 32 N 126 I
ΔΕ=+1.6
Δn=0.373
γ₁=1269 mPa·s Comparative Example 4

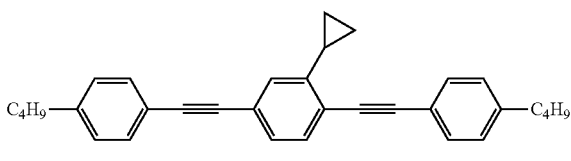

C 72 N 84.5 I
ΔΕ=+1.5
Δn=0.378
γ₁=2194 mPa·s

Synthesis Example 9

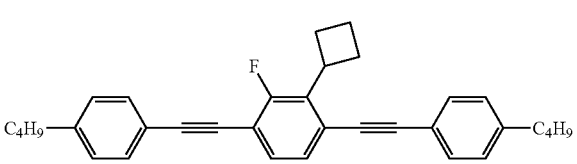

The title compound is prepared analogously to Example 1.
C 60 N 89 I
ΔΕ=+1.3
Δn=0.348
γ₁=1875 mPa·s Comparative Example 5

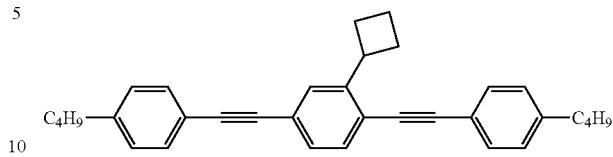

Tg −39 C 69 N 70 I
ΔΕ 0.9
Δn 0.359
γ₁ 3067 mPa·s

Synthesis Example 10

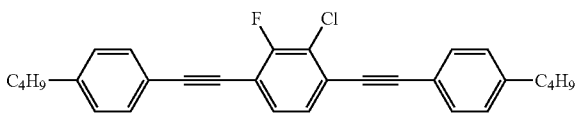

The title compound is prepared analogously to Example 1.
C 80 N 192 I
ΔΕ=−0.9
Δn=0.426
γ₁=508 mPa·s Synthesis Example 11

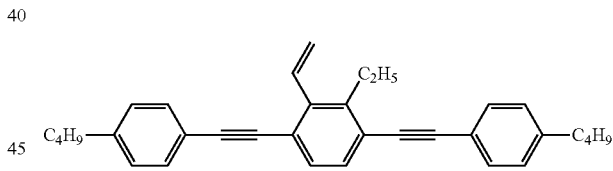

The title compound is prepared analogously to Example 1.
C 41 N 161 I
ΔΕ=2.4
Δn=0.437

Synthesis Example 12

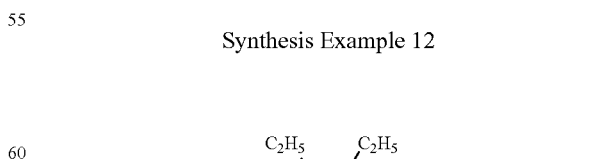

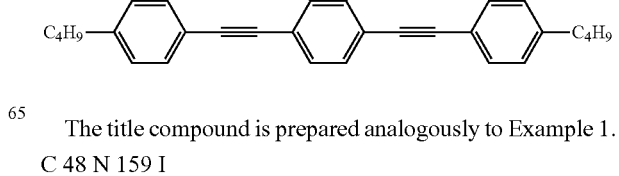

The title compound is prepared analogously to Example 1.
C 48 N 159 I

Synthesis Example 13

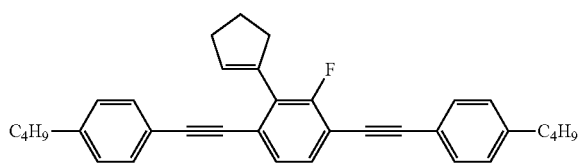

The title compound is prepared analogously to Example 1.
Tg −37 C 52 N 78 I
Δε=0.9
Δn=0.339
γ₁=2219 mPa·s

Synthesis Example 14

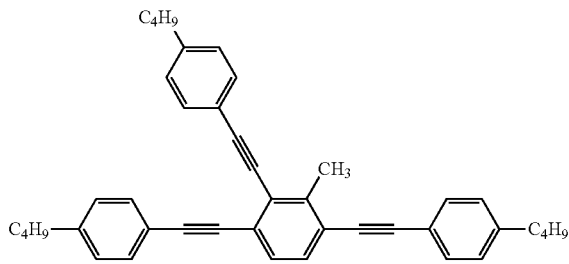

The title compound is prepared analogously to Example 1.
Tg −34 C 72 N (49) I
Δε=0.8
Δn=0.302
γ₁=785 mPa·s

Synthesis Example 15

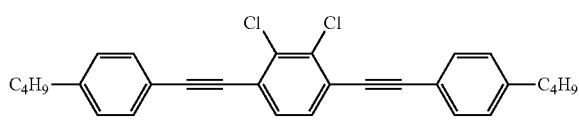

The title compound is prepared analogously to Example 1.
C 97 N 204 I
Δε=−0.9
Δn=0.421
γ₁=610 mPa·s

Synthesis Example 16

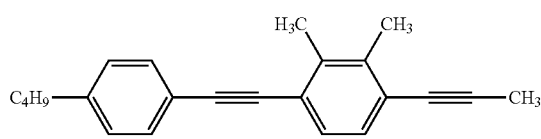

The title compound is prepared analogously to Example 1.
C 72 N (51) I

Mixture Example 1

A liquid-crystal medium M-1 having the composition and properties as indicated in the following table is prepared. Compound (1) (No. 15) originates from Synthesis Example 8.

| Composition | | |
|---|---|---|
| Compound | | |
| No. | Abbreviation | |
| 1 | BCH-3F.F | 10.8% |
| 2 | BCH-5F.F | 9.00% |
| 3 | ECCP-30CF3 | 4.50% |
| 4 | ECCP-50CF3 | 4.50% |
| 5 | CBC-33F | 1.80% |
| 6 | CBC-53F | 1.80% |
| 7 | CBC-55F | 1.80% |
| 8 | PCH-6F | 7.20% |
| 9 | PCH-7F | 5.40% |
| 10 | CCP-20CF3 | 7.20% |
| 11 | CCP-30CF3 | 10.8% |
| 12 | CCP-40CF3 | 6.30% |
| 13 | CCP-50CF3 | 9.90% |
| 14 | PCH-5F | 9.00% |
| 15 | (1) | 10.0% |
| Σ | | 100.0% |
| Physical properties | | |
| T(N, I) = | | 96° C. |
| Δn (20° C., 589.3 nm) = | | 0.124 |
| Δε (20° C., 1 kHz) = | | 4.9 |
| γ₁ (20° C.) = | | 166 mPa · s |

This mixture is used for applications in the microwave range, in particular for phase shifters for 'phased array' antennae.

For comparison, a medium C-1 without component (1) is prepared from compound Nos. 1-14 of medium M-1, where compound Nos. 1-14 are present in the same relative amounts.

TABLE

Properties of mixtures M-1 and C-2 (comparison) at 19 GHz (20° C.)

| Mixture | $\epsilon_{r,\|\|}$ | $\epsilon_{r,\perp}$ | τ | tan $\delta_{\epsilon,r,\|\|}$ | tan $\delta_{\epsilon,r,\perp}$ | η |
|---|---|---|---|---|---|---|
| M-1 | 2.57 | 2.33 | 0.097 | 0.0044 | 0.0130 | 7.41 |
| C-1 | 2.49 | 2.30 | 0.079 | 0.0048 | 0.0139 | 5.70 |

The tuneability τ and the material quality η are improved compared with comparative mixture C-1.

Further combinations of the embodiments and variants of the invention in accordance with the description also arise from the following claims.

The invention claimed is:

1. A compound of the formula I

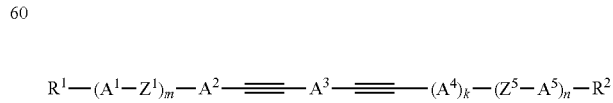

in which
A³ denotes

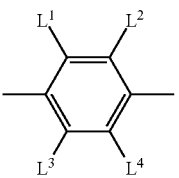

L¹ denotes branched or unbranched alkyl, alkenyl or alkynyl having 1 to 12 C atoms, in which, in addition, one or more —CH$_2$— groups may be replaced, independently of one another, by O, substituted or unsubstituted cycloalkyl, cycloalkenyl, substituted or unsubstituted phenyl, substituted or unsubstituted arylethynyl, fluorinated alkyl or alkenyl, or fluorinated alkoxy or alkenyloxy, or L¹ denotes F, Cl, Br, CN, NCS or SF$_5$, L² denotes branched or unbranched alkyl, alkenyl or alkynyl having 1 to 12 C atoms, in which, in addition, one or more —CH$_2$— groups may be replaced, independently of one another, by O, substituted or unsubstituted cycloalkyl, cycloalkenyl, substituted or unsubstituted phenyl, substituted or unsubstituted arylethynyl, fluorinated alkyl or alkenyl, fluorinated alkoxy or alkenyloxy, L³ and L⁴ independently are as defined for L¹ or denote H, R¹ and R², independently of one another, denote a halogenated or unsubstituted alkyl radical having 1 to 15 C atoms, where, in addition, one or more CH$_2$ groups in these radicals may each be replaced, independently of one another, by —C≡C—, —CH═CH—, —CF═CF—, —CF═CH—, —CH═CF—, —(CO)— and —O— in such a way that O atoms are not linked directly to one another, or denote F, Cl, Br, CN, CF$_3$, OCF$_3$, NCS or SF$_5$, or R² can also denote H, A¹, A², A⁴ and A⁵ each, independently of one another, denote
a) 1,4-phenylene, in which one or more CH groups may be replaced by N,
b) trans-1,4-cyclohexylene or cyclohexenylene, in which, in addition, one or two non-adjacent CH$_2$ groups may be replaced by —O— and/or —S—, and in which H may be replaced by F,
c) a radical of the formula

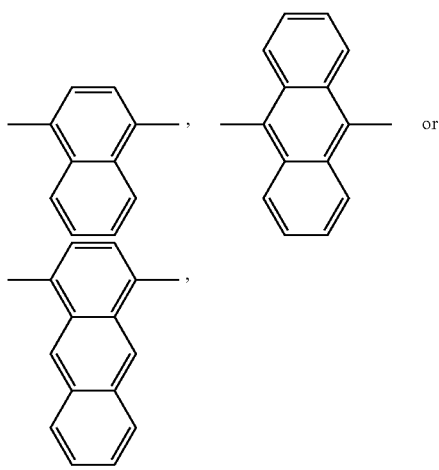

d) a radical selected from 1,4-bicyclo[2.2.2]octylene, cyclo-butane-1,3-diyl, spiro[3.3]heptane-2,6-diyl, thiophene-2,5-diyl, thiophene-2,4-diyl, furan-2,5-diyl, furan-2,4-diyl,

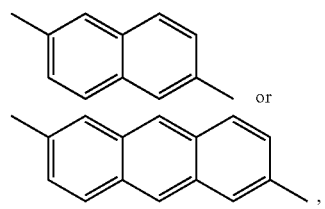

and in which, in groups a), b), c) and d),
one or more H atoms may, in addition, be replaced by Br, Cl, F, CN, —NCS, —SCN, SF$_5$, C$_1$-C$_{10}$ alkyl, C$_1$-C$_{10}$ alkoxy or a mono- or polyfluorinated C$_1$-C$_{10}$ alkyl or alkoxy group, k denotes 0 or 1, Z¹ and Z⁵, independently of one another, denote a single bond, —C≡C—, —CH═CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH═CF— or —CF═CF—, where asymmetrical bridges may be oriented to both sides, where, for k=0, Z⁵ is a single bond, and m and n, independently of one another, denote 0, 1 or 2.

2. A compound according to claim 1, wherein L³ and L⁴ both denote H or both do not denote H.

3. A compound according to claim 1, wherein L¹ denotes F.

4. A compound according to claim 1,
wherein L¹ and/or L² independently denote
a halogenated or unsubstituted alkyl radical having 1 to 12 C atoms, where, in addition, one or more CH$_2$ groups in these radicals may each be replaced, independently of one another, by —C≡C—, —CH═CH—, —CF═CF—, —CF═CH—, —CH═CF—, —(CO)O—, —O(CO)—, —(CO)—, —O— or —S— in such a way that O or S atoms are not linked directly to one another, optionally alkyl-substituted cycloalkyl having 3 to 6 C atoms, or optionally halogen-, C$_{1-6}$-alkyl- or C$_{1-6}$-alkoxy-substituted phenyl.

5. A compound according to claim 1, wherein m and n are 0.

6. A compound according to claim 1, wherein k is 1.

7. A liquid-crystal medium, which comprises one or more compounds of the formula I according to claim 1.

8. A liquid-crystal medium according to claim 7, which additionally comprises one or more compounds selected from the compounds of the formula II:

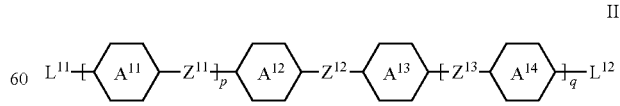

in which:
L¹¹ denotes R¹¹ or X¹¹,
L¹² denotes R¹² or X¹²,
R¹¹ and R¹², independently of one another, denote unfluorinated alkyl or unfluorinated alkoxy having 1 to 17 C atoms or unfluorinated alkenyl, unfluorinated alkynyl, unfluorinated alkenyloxy or unfluorinated alkoxyalkyl having 2 to 15 C atoms, $X^{11}$ and $X^{12}$, independently of one another, denote F, Cl, Br, —CN, —NCS, —SCN, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, p and q independently denote 0 or 1, $Z^{11}$ to $Z^{13}$, independently of one another, denote trans-CH=CH—, trans-CF=CF—, —C≡C— or a single bond, and

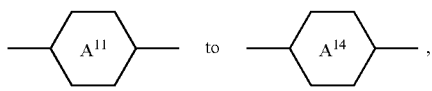

independently of one another, denote

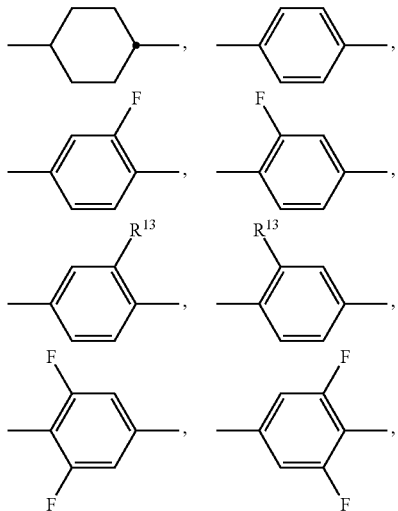

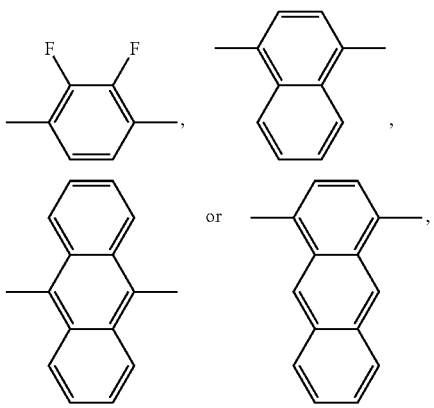

where $R^{13}$ denotes Cl, $C_{1-5}$ alkyl, $C_{1-5}$ alkenyl or $C_{3-6}$ cycloalkyl.

9. A liquid-crystal medium according to claim 7, wherein the concentration of the compounds of the formula I in the medium is in the range from in total 5% to 95%.

10. A component for high-frequency technology, comprising at least one compound of the formula I according to claim 1.

11. A process for the preparation of a liquid-crystal medium according to claim 7, which comprises mixing one or more compounds of the formula I with one or more further compounds and optionally with one or more additives.

12. A component for high-frequency technology, which comprises a liquid-crystal medium according to claim 7.

13. A component according to claim 12, which is one or more functionally connected phase shifters.

14. A phased array antenna which comprises one or more components according to claim 12.

* * * * *